United States Patent
Krill et al.

(10) Patent No.: US 9,809,530 B2
(45) Date of Patent: Nov. 7, 2017

(54) METHOD FOR PRODUCING ALPHA-HYDROXY CARBOXYLIC ESTERS IN THE GAS PHASE

(71) Applicants: Steffen Krill, Muehltal (DE); Belaid Ait Aissa, Darmstadt (DE); Alexander May, Seeheim-Jugenheim (DE); Matthias Groemping, Darmstadt (DE)

(72) Inventors: Steffen Krill, Muehltal (DE); Belaid Ait Aissa, Darmstadt (DE); Alexander May, Seeheim-Jugenheim (DE); Matthias Groemping, Darmstadt (DE)

(73) Assignee: Evonik Roehm GmbH, Darmstadt (DE)

( * ) Notice: Subject to any disclaimer, the term of this patent is extended or adjusted under 35 U.S.C. 154(b) by 0 days.

(21) Appl. No.: 15/323,888

(22) PCT Filed: Jul. 23, 2015

(86) PCT No.: PCT/EP2015/066819
§ 371 (c)(1),
(2) Date: Jan. 4, 2017

(87) PCT Pub. No.: WO2016/016073
PCT Pub. Date: Feb. 4, 2016

(65) Prior Publication Data
US 2017/0144960 A1    May 25, 2017

(30) Foreign Application Priority Data
Aug. 1, 2014 (EP) .................................. 14179444

(51) Int. Cl.
*C07C 67/20* (2006.01)
*B01J 21/06* (2006.01)
*C01C 1/08* (2006.01)
*C01C 3/02* (2006.01)

(52) U.S. Cl.
CPC ............. *C07C 67/20* (2013.01); *B01J 21/066* (2013.01); *C01C 1/08* (2013.01); *C01C 3/02* (2013.01)

(58) Field of Classification Search
CPC ....... C07C 67/20; C07C 69/675; C07C 67/62; B01J 21/066; C01C 1/08; C01C 3/02; C01C 3/0229; Y02P 20/58
See application file for complete search history.

(56) References Cited

U.S. PATENT DOCUMENTS

| 4,161,609 A | 7/1979 | Cramer |
| 2009/0209781 A1 | 8/2009 | Ackermann et al. |
| 2012/0095253 A1 | 4/2012 | Matsuda et al. |

FOREIGN PATENT DOCUMENTS

| EP | 2 415 750 A1 | 2/2012 |
| WO | 2008/009503 A1 | 1/2008 |

OTHER PUBLICATIONS

International Search Report dated Aug. 13, 2015 in PCT/EP2015/066819 filed Jul. 23, 2015.
European Search Report dated Jan. 21, 2015 in European Application 14 17 9444.6 filed Aug. 1, 2014.

*Primary Examiner* — Yevegeny Valenrod
*Assistant Examiner* — Blaine G Doletski
(74) *Attorney, Agent, or Firm* — Oblon, McClelland, Maier & Neustadt, L.L.P.

(57) ABSTRACT

The present invention relates to a process for preparing alpha-hydroxycarboxylic esters from the alcoholysis of alpha-hydroxycarboxamides in the gas phase, characterized in that the conversion is effected in the presence of water.

6 Claims, No Drawings

METHOD FOR PRODUCING ALPHA-HYDROXY CARBOXYLIC ESTERS IN THE GAS PHASE

The present invention relates to a process for preparing alpha-hydroxycarboxylic esters (HCEs) by alcoholysis of the corresponding alpha-hydroxycarboxamides (HCAs) in the gas phase.

The preparation of HCEs by means of alcoholysis of HCAs is sufficiently well known from the prior art. DE 2454497 describes a corresponding reaction using lead compounds as catalyst. In this context, continuous process variants are also mentioned, but without providing a technical solution in which the products are obtained with a high efficiency.

DE 2528524 describes a process for preparing HCEs using catalysts including lanthanum compounds inter alia. Here too, it is mentioned that the processes can be conducted continuously but without providing satisfactory solutions for the problems that occur in long-term operation.

EP 0945423 discloses a process for preparing HCEs, wherein an HCA is reacted with an alcohol in the presence of a catalyst in a liquid phase, while the ammonia concentration in the reaction solution is kept at ≤0.1% by weight. Therefore, ammonia formed is constantly removed very substantially from the reaction solution. For this purpose, the reaction solution is heated to boiling, and a stripping gas is bubbled through the reaction solution. The disadvantages of the existing process are that effective removal of the ammonia requires an extremely effective separation column and hence an exceptional level of technical complexity.

The use of an inert stripping gas does improve the ammonia removal, but at the cost of a further process component, the workup of which means additional handling. Moreover, if alpha-hydroxyisobutyramide and methanol are used as corresponding reactants, ammonia and residual methanol formed under the conditions indicated in the publication can be separated from one another only with very great difficulty. The additional handling of a further stream (separation of stripping gas/ammonia) which is also necessary means that the procedure proposed is of relatively little economic interest, and so this process has to date not been implemented in industry. In the case of this catalytic execution in the liquid phase, there is additionally formation of by-products, for example N-methylhydroxyisobutyramide or trimethylamine, which have to be removed from the desired methyl hydroxyisobutyrate product by appropriate processes in a very complex manner.

Recently, EP 2415750 disclosed a process which describes the alcoholysis of HCAs in the gas phase. It is shown here that significantly higher conversions up to 90% of HCAs can be achieved "per single path", which already leads to a significant improvement in steam consumption in the preparation of HCE, since smaller circulation streams are obtained. It is found, however, that the selectivities for HCE are much poorer and there is increased occurrence of by-products, for example acetone and 2-amino-2-methylpropionitrile (AMPN). Thus, the gas phase process described therein can be assessed as being better in energetic terms than the processes in the liquid phase, but the selectivities are unsatisfactory, and the resulting relatively high concentration of by-products is disadvantageous in some cases for long-term operation.

In view of the prior art, the problem addressed by the present invention was that of providing processes for preparing HCEs, which can be conducted in an energy- and resource-conserving manner and hence easily and inexpensively. A further problem addressed by the invention was that of providing a process in which HCEs can be obtained very selectively. Another problem addressed by the present invention was that of providing a process for preparing HCEs, in which no by-products or only small amounts of by-products are produced. At the same time, the product should as far as possible be obtained in high yields and, viewed overall, with low energy consumption. These problems, and further problems which have not been stated explicitly, are solved by providing a process for preparing HCEs by alcoholysis of the corresponding HCA in the gas phase over a heterogeneous catalyst, characterized in that the molar ratio of alcohol to HCA is 2-25 mol/mol and the conversion is effected in the presence of water.

HCAs usable in the reaction of the invention typically include all those carboxamides that bear at least one hydroxyl group in the alpha position to the carboxamide group.

Carboxamides in turn are common knowledge in the art. These are typically understood to mean compounds bearing groups having the formula —CONR'R"— in which R' and R" are each independently hydrogen or a group comprising 1-30, more particularly 1-20, preferably 1-10 and more particularly 1-5 carbon atoms, particular preference being given to amides where R' and R" are hydrogen. The carboxamide may bear 1, 2, 3, 4 or more groups having the formula —CONR'R"—. These include in particular compounds having the formula R(—CONR'R")$_n$ where the radical R is a group comprising 1-30, more particularly 1-20, preferably 1-10, more particularly 1-5 and more preferably 2-3 carbon atoms, R' and R" are as defined above and n is an integer in the range of 1-10, preferably 1-4 and more preferably is 1 or 2.

The expression "group comprising 1 to 30 carbon atoms" denotes radicals of organic compounds having 1 to 30 carbon atoms. It includes not only aromatic and heteroaromatic groups but also aliphatic and heteroaliphatic groups, for example alkyl, cycloalkyl, alkoxy, cycloalkoxy, cycloalkylthio and alkenyl groups. These latter groups may be branched or unbranched.

According to the invention, aromatic groups are radicals of mono- or polycyclic aromatic compounds preferably comprising 6 to 20, more particularly 6 to 12, carbon atoms.

Heteroaromatic groups are aryl radicals in which at least one CH group has been replaced by N and/or at least two adjacent CH groups have been replaced by S, NH or O.

Aromatic or heteroaromatic groups preferred in accordance with the invention derive from benzene, naphthalene, biphenyl, diphenyl ether, diphenylmethane, diphenyldimethylmethane, bisphenone, diphenyl sulphone, thiophene, furan, pyrrole, thiazole, oxazole, imidazole, isothiazole, isoxazole, pyrazole, 1,3,4-oxadiazole, 2,5-diphenyl-1,3,4-oxadiazole, 1,3,4-thiadiazole, 1,3,4-triazole, 2,5-diphenyl-1,3,4-triazole, 1,2,5-triphenyl-1,3,4-triazole, 1,2,4-oxadiazole, 1,2,4-thiadiazole, 1,2,4-triazole, 1,2,3-triazole, 1,2,3,4-tetrazole, benzo[b]thiophene, benzo[b]furan, indole, benzo[c]thiophene, benzo[c]furan, isoindole, benzoxazole, benzothiazole, benzimidazole, benzisoxazole, benzisothiazole, benzopyrazole, benzothiadiazole, benzotriazole, dibenzofuran, dibenzothiophene, carbazole, pyridine, bipyridine, pyrazine, pyrazole, pyrimidine, pyridazine, 1,3,5-triazine, 1,2,4-triazine, 1,2,4,5-triazine, tetrazine, quinoline, isoquinoline, quinoxaline, quinazoline, cinnoline, 1,8-naphthyridine, 1,5-naphthyridine, 1,6-naphthyridine, 1,7-naphthyridine, phthalazine, pyridopyrimidine, purine, pteridine or quinolizine, 4H-quinolizine, diphenyl ether, anthracene, benzopyrrole, benzooxathiadiazole, benzoxadiazole, benzo-pyridine, benzopyrazine, benzopyrazidine, benzopyrimidine, benzotriazine, indolizine, pyridopyridine, imidazopyrimidine, pyrazinopyrimidine, carbazole, acridine, phenazine, benzoquinoline, phenoxazine, phenothiazine, acridizine, benzopteridine, phenanthroline and phenanthrene, any of which may optionally also be substituted.

Preferred alkyl groups include methyl, ethyl, propyl, isopropyl, 1-butyl, 2-butyl, 2-methylpropyl, tert-butyl, pentyl, 2-methylbutyl, 1,1-dimethylpropyl, hexyl, heptyl, octyl, 1,1,3,3-tetramethylbutyl, nonyl, 1-decyl, 2-decyl, undecyl, dodecyl, pentadecyl and eicosyl.

Preferred cycloalkyl groups include cyclopropyl, cyclobutyl, cyclopentyl, cyclohexyl, cycloheptyl and cyclooctyl, any of which are optionally substituted by branched or unbranched alkyl groups.

Preferred alkenyl groups include vinyl, allyl, 2-methyl-2-propenyl, 2-butenyl, 2-pentenyl, 2-decenyl and 2-eicosenyl.

Preferred heteroaliphatic groups include the aforementioned preferred alkyl and cycloalkyl radicals in which at least one carbon unit has been replaced by O, S or an $NR^8$ or $NR^8R^9$ group and $R^8$ and $R^9$ are each independently an alkyl group having 1 to 6 carbon atoms, an alkoxy group having 1 to 6 carbon atoms or an aryl group.

It is most preferable in accordance with the invention when the carboxamides bear branched or unbranched alkyl or alkoxy groups comprising 1 to 20 carbon atoms, preferably 1 to 12, advantageously 1 to 6 and in particular 1 to 4 carbon atoms, and cycloalkyl or cycloalkyloxy groups comprising 3 to 20 carbon atoms, preferably 5 to 6 carbon atoms.

The R radical may bear substituents. Preferred substituents include halogens, especially fluorine, chlorine, bromine, and also alkoxy or hydroxyl radicals.

The HCAs may be used in the process of the invention individually or as a mixture of two or three or more different HCAs. Particularly preferred HCAs include alpha-hydroxyisobutyramide and/or alpha-hydroxyisopropionamide.

It is further of particular interest in one form of the process according to the invention to use HCAs obtainable from ketones or aldehydes and hydrogen cyanide by cyanohydrin synthesis. The first step of said synthesis comprises reacting the carbonyl compound, for example a ketone, particularly acetone, or an aldehyde, for example acetaldehyde, propanal, butanal, with hydrogen cyanide to afford the particular cyanohydrin. It is particularly preferable when said synthesis comprises reacting acetone and/or acetaldehyde in typical fashion in the presence of a small amount of alkali or an amine as catalyst. In a further step, the cyanohydrin thus obtained is reacted with water to afford the HCAs.

Alcohols usable successfully in processes of the invention include any alcohols familiar to those skilled in the art and also alcohol precursor compounds capable of undergoing an alcoholysis-type reaction with the HCAs under the stated conditions of pressure and temperature. The reaction of the HCA is preferably carried out by alcoholysis with an alcohol preferably comprising 1-10 carbon atoms, more preferably comprising 1 to 5 carbon atoms. Preferred alcohols include methanol, ethanol, propanol, butanol, particularly n-butanol and 2-methyl-1-propanol, pentanol, hexanol, heptanol, 2-ethylhexanol, octanol, nonanol and decanol and mixtures thereof. It is particularly preferable when the alcohol employed is methanol and/or ethanol, methanol being most advantageous. The use of precursors of an alcohol is also possible in principle. It is thus possible to use alkyl formates for example. Methyl formate or a mixture of methanol and carbon monoxide are particularly suitable.

Also preferred are processes characterized in that the HCA used is hydroxyisobutyramide (HIBA) and the alcohol used is methanol, in which case these compounds react to afford the target product methyl hydroxyisobutyrate (MHIB).

Suitable catalysts for the process according to the invention are zirconium dioxides doped with elements from groups 2-4, 7 or 9-13 of the periodic table or with La, Sb, or Bi. Undoped zirconium dioxides are also suitable. Preferred dopant elements for zirconium dioxide are those from groups 3, 7, 9, 10 or 13 of the periodic table or are selected from the group consisting of B, Al, Mn, Co, Ni, Y, La or Yb. Particular preference is given to the dopant elements Ce, K, La, Mo, P, S, Si, Ti, W, Y and Zn, greatest preference being given to Ce, K or La. The dopant content is 0-50%, preferably 0.2-20% and more preferably 0.4-15% by weight.

The process according to the invention is a gas phase reaction, the heterogeneous catalyst being in the form of a fixed bed, moving bed or fluidized bed. Suitable apparatus solutions for configuration of the catalyst bed are described in Ullmann's Encyclopedia of Industrial Chemistry, Wiley 2012, p 293 ff. (DOI: 10.1002/14356007.b04_087).

In the inventive gas phase reaction, higher conversions are achieved compared to the liquid phase reaction, since the reaction equilibrium is shifted more strongly from the reactants toward the products in the gas phase. In the context of the present invention, "gas phase reaction" should be understood such that the reaction proceeds essentially in the gas phase, the proportion of the liquid phase present being <10%, preferably <5%, more preferably <2% and most preferably 0% by weight, based on the total amount of the reactants.

The HCA and alcohol reactants may be converted to the gas phase before being fed into the reactor or within the reactor itself. In addition, the reactants can be fed to the reactor separately or as a mixture. The reaction can in principle also be conducted in the presence of an inert gas, for example nitrogen, which facilitates the conversion of the reactants to the gas phase because of the lowering of the partial pressures of the reactants. However, the preferred variant does not need inert gas, since the labour involved in additional handling of inert gas is thus dispensed with. Preferred reactor types are tubular reactors.

For separation of the reaction products formed from unconverted reactants, by-products and/or other components, customary processes known to those skilled in the art may be employed, for example rectification.

The reaction temperature is chosen such that there is sufficient evaporation of the reactants, which depends essentially on the nature of the reactants and the reaction pressure chosen. In the preferred process for reaction of HIBA with methanol, the reaction temperature is 150-300° C., preferably 160-250° C., more preferably 180-230° C.

The reaction pressure in the reaction of HIBA with methanol is 0.1-3 bar, preferably 0.2-3 bar, more preferably 0.3-1.5 bar.

The gas phase process according to the invention is conducted in the presence of water. It has been found that, surprisingly, for example in the case of reaction of HIBA with methanol in the presence of water, the formation of by-products, especially acetone or 2-amino-2-methylpropionitrile (AMPN), is suppressed very significantly, and the selectivity for MHIB and the catalyst service life are substantially increased. Water can either be added to the reactant feed or fed directly into the reactor. The molar ratio of water to HCA is 0.1-10, preferably 0.3-5 and more preferably 0.5-1 mol/mol.

The molar ratio of alcohol to HCA is 2-25, preferably 7-20 and more preferably 10-15 mol/mol.

The WHSV (weight hourly space velocity) based on HCA is 0.05-2, preferably 0.1-1.5, more preferably 0.1-0.6 h$^{-1}$.

In a further preferred variant of the process according to the invention, the reactant streams are treated with a cationic ion exchanger prior to evaporation. This may be necessary when, in the case of use of catalytic processes which are used in the preparation of the precursors of the hydroxycarboxylic acids, metal ions from the catalysts used or secondary auxiliaries remain in the feedstock for the methanolysis. Thus, in the case of preparation of hydroxyisobutyramide proceeding from acetone cyanohydrin by means of hydrolysis over heterogeneous manganese dioxide-based catalysts, the auxiliary, namely the pH stabilizer (usually an alkali metal hydroxide, preferably lithium, sodium or potassium), may remain in the product even after the workup; thus, these alkali traces in the subsequent gas phase methanolysis would lead to caking in the evaporator, any traces that get to the catalyst would damage it, or else they would exert a general adverse effect on the reaction in the course of evaporation and catalysis. The same relationships apply to other mineral substances which get into the hydroxycarboxylic acid used as reactant in traces from the precursor(s), for example manganese ions (from the manganese dioxide catalyst) and $SiO_2$ (is used as an auxiliary in manganese dioxide preparation), to name just a few impurities by way of example.

This serves primarily to eliminate metal compounds which have possibly leached out of the catalyst, especially those of the alkali metal or alkaline earth metal ions, from the feed. More particularly, metal compounds from groups I A, II A, IV A of the Periodic Table of the Elements, and of the transition elements, especially of group VII B, are used. Suitable treatment steps with ion exchangers are sufficiently well known from the prior art. Suitable ion exchangers are, for example, those marketed by Rohm & Haas under the trade name Amberlyst. It has been found that, surprisingly, especially in the case of reaction of HIBA with methanol to give MHIB, it is thus possible to reduce or completely avoid deposit formation or any tendency to blockage in the evaporation region of the plant. The pH of the reactant streams after passage through the ion exchanger is 3-7.

As an alternative to the pretreatment of the feed with an ion exchanger, the evaporator used upstream of the reactor, in which the entire feed is evaporated, may be replaced by a partial evaporator, from which a high boiler fraction containing said metal impurities from the catalyst is discharged. The high boiler fraction discharged in this case is 0.1-20%, preferably 0.2-10% and more preferably 0.5-5% by weight, based on the overall feed. If necessary, the high boiler fraction discharged can be subjected to a downstream further evaporation step, in which case the low boilers are fed back to the aforementioned partial evaporator. It is also possible here to use other methods known to those skilled in the art, in order to recover further starting material.

The ammonia released in the preferred variants of the process of the present invention may be recycled, for example, into a hydrogen cyanide preparation process. For example, ammonia can be reacted with methanol to give hydrogen cyanide. This is detailed, for example, in EP 0941984. In addition, the hydrogen cyanide can be obtained from ammonia and methane by the BMA or Andrussow process, these processes being described in Ullmann's Encyclopedia of Industrial Chemistry 5th edition, 1995, on CD-ROM, under "Inorganic Cyano Compounds". It is likewise possible to recycle the ammonia to an ammoxidation process, for example the industrial scale synthesis of acrylonitrile from ammonia, oxygen and propene. Acrylonitrile synthesis is described under "Sohio process" in Industrial Organic Chemistry, 1997, by K. Weissermel and H.-J. Arpe on pages 307 ff.

If necessary, ammonia released is introduced into aforementioned hydrogen cyanide or ammoxidation processes after a purification step which especially includes solid adsorbents. A useful solid adsorbent is more preferably activated carbon.

Activated carbon can be used in all possible morphological forms, in powder form, in granulated form, or as cylindrical or spherical pellets. Preference is given to granulated activated carbons having surface values of 1000-1500 m$^2$/g, more preferably 1200-1400 m$^2$/g. As well as activated carbon activated chemically with zinc chloride or phosphoric acid, activated carbons which have been gas-activated using alkali metal salts, alkali metals, chlorides, sulphates and acetates are preferred.

Possible adsorbers are fixed bed, moving bed or fluidized bed adsorbers. Illustrative apparatus solutions are described, for example, in Ullmann's Encyclopedia of Industrial Chemistry, Wiley 2012, p 293 ff. (DOI: 10.1002/14356007.b04_087). The procedure can be effected continuously or batchwise, preference being given to the former.

The adsorption is conducted within a temperature range of 0-150° C., preferably of 30-100° C., more preferably of 35-50° C., and at pressures of 0.1-5 bar, preferably at 0.5-4 bar, more preferably at 1-3 bar.

The process according to the invention also includes the regeneration of the alcoholysis catalyst. This is effected with a medium at 200-600° C., preferably at 350-500° C.

Suitable regeneration media are air, water vapour, inert gases, for example nitrogen, argon, xenon, or combustion gases, for example $CO_2$ or nitrogen oxides, and mixtures thereof. The laden or exhausted regeneration media may be supplied to suitable customary disposal processes, for example to a biological treatment plant or a thermal oxidizer.

The regeneration can be conducted under either reductive or oxidative conditions, and its effect is essentially that the acid-base properties of the fresh catalyst are restored.

The regeneration temperatures are 200-600° C., preferably 300-500° C., more preferably 350-450° C.

The regeneration time is 1-24 h, preferably 2-18 h, more preferably 3-12 h.

The WHSV (weight hourly space velocity) of the regeneration medium over the catalyst to be regenerated is 0.01-10, preferably 0.1-5, more preferably 0.4-1.5 h$^{-1}$.

The examples which follow are intended to illustrate but not in any way restrict the invention.

COMPARATIVE EXAMPLES 1-4

A solution of 20% by weight of HIBA in methanol is fed by means of an HPLC pump (Knauer) with a flow rate of 1 g/min into an evaporator consisting of a stainless steel capillary tube of length 1 m wound around a 500 W heating cylinder. The gas mixture that arises is passed into a fixed bed reactor of length 33 cm and internal diameter 1 cm. The catalyst charge consists of 100 g of yttrium-doped zirconium dioxide (dopant concentration 8.3% by weight). The corresponding WHSV based on HIBA is 0.2 h$^{-1}$. The results in terms of conversion and selectivity of the experiments conducted at four different reactor temperatures, each at a reaction pressure of 400 mbar, are listed in Tab. 1.

TAB. 1

Conversion and selectivity at various temperatures without water

| Comparative Example | Reaction temperature/ °C. | HIBA conversion/ % | Selectivity/% | | | | |
|---|---|---|---|---|---|---|---|
| | | | Acetone | MMA | HIBAc | AMPN | MHIB |
| 1 | 220 | 80 | 1 | 0 | 1 | 8 | 90 |
| 2 | 240 | 86 | 3 | 1 | 2 | 12 | 82 |
| 3 | 260 | 91 | 5 | 2 | 4 | 18 | 71 |
| 4 | 280 | 94 | 10 | 4 | 2 | 23 | 54 |

HIBAc = hydroxyisobutyric acid
MMA = methyl methacrylate

When the reaction temperature is increased by 60° C., the conversion of HIBA increases from 80% to 94%. At the same time, the selectivity for the desired MHIB target product decreases from 90% to 54%, and the selectivity for, for example, the unwanted AMPN by-product rises from 8% to 23%. Without the addition or presence of water (according to the Mitsubishi Gas Chem. patent publication EP 2415750), no optimization point is found that reduces by-production of AMPN, reduces acetone elimination from hydroxyisobutyramide and achieves selectivities >93%.

EXAMPLES 1-9

Examples 1-9 were conducted in the same apparatus as Comparative Examples 1-4. However, 1% by weight of water was added to the feed at the expense of methanol. The reaction temperature was 220° C. The results in terms of HIBA conversion and MHIB selectivity for zirconium dioxide catalysts doped with various oxides are shown in Tab. 2.

TAB. 2

Various zirconium dioxide catalysts with 1% water

| Example | Doping/ % by wt. | Dopant | Pore volume/ cm³/g | Surface area/ m²/g | HIBA conversion/ % | MHIB selectivity/ % |
|---|---|---|---|---|---|---|
| 1 | 18.83 | CeO$_2$ | 0.27 | 101 | 97.7 | 96.5 |
| 2 | 0.43 | K$_2$O | 0.35 | 86.5 | 96.7 | 96.5 |
| 3 | 9.7 | La$_2$O$_3$ | 0.29 | 106 | 96.4 | 95.9 |
| 4 | 8.8 | La$_2$O$_3$ | 0.28 | 100 | 96.6 | 94.7 |
| 5 | 4.5 | Y$_2$O$_3$ | 0.28 | 114 | 96.9 | 93.7 |
| 6 | — | — | 0.3 | 103 | 96 | 92.2 |
| 7 | 12.6 | P$_2$O$_5$ | 0.17 | 140 | 96.2 | 91.6 |
| 8 | 7.3 | ZnO | — | — | 96.3 | 91.6 |
| 9 | 8.3 | Y$_2$O$_3$ | 0.26 | 115 | 97.9 | 91.1 |

What are noticeable are the distinctly elevated conversions and selectivities compared to Comparative Examples 1-4 without water in the feed. Particularly good values are exhibited by the Ce-, K- and La-doped catalysts.

Even the small catalytic co-feed of water, under otherwise similar or identical reaction conditions, effectively suppresses the elimination of acetone and drastically reduces the production of the unwanted AMNP by-product. Thus, the product selectivity is significantly enhanced.

COMPARATIVE EXAMPLES 5-9

Comparative Example 1 was repeated, except at a reaction pressure of 1013 mbar and, as shown in Tab. 3, at different ratios of methanol/water to HIBA. The results for Comparative Example 9 are shown in Tab. 4.

TAB. 3

Different feed compositions

| Comparative Example | Molar ratios/mol/mol | | | | HIBA conversion/ % | Selectivity/% | | | |
|---|---|---|---|---|---|---|---|---|---|
| | MeOH/ (MeOH + H$_2$O) | MeOH / HIBA | H$_2$O/ HIBA | (MeOH + H$_2$O)/ HIBA | | MHIB | Acetone | HIBAc | MAA |
| 5 | 0.00 | 0.00 | 13.00 | 13.00 | 54.40 | 0.00 | 0.29 | 94.27 | 5.34 |
| 6 | 0.07 | 0.99 | 12.38 | 13.38 | 57.11 | 11.73 | 0.51 | 80.37 | 4.89 |
| 7 | 0.15 | 1.98 | 11.30 | 13.28 | 58.16 | 22.92 | 0.51 | 67.30 | 4.48 |
| 8 | 0.27 | 3.37 | 9.09 | 12.47 | 56.44 | 33.98 | 0.56 | 59.95 | 3.88 |

MAA = methacrylic acid

As expected, no MHIB is formed in the absence of methanol. Below a molar ratio of methanol to HIBA of 4, no significant amounts of MHIB form even in the presence of water.

EXAMPLES 10-12 AND COMPARATIVE EXAMPLE 9

Comparative Example 5 was repeated with the feed compositions shown in Tab. 4.

TAB. 4

Different feed compositions with and without water

| Example/ Comp. Example | Molar ratios/mol/mol | | | HIBA conversion/ % | Selectivity/% | | | | | |
|---|---|---|---|---|---|---|---|---|---|---|
| | MeOH/ (MeOH + H₂O) | MeOH / HIBA | H₂O/ HIBA | (MeOH + H₂O)/ HIBA | | MHIB | Acetone | AMPN | HIBAc | MMA | MAA |
| 10 | 0.38 | 5.12 | 8.23 | 13.35 | 85.84 | 87.27 | 0.64 | 0.00 | 7.89 | 0.00 | 0.65 |
| 11 | 0.57 | 7.65 | 5.74 | 13.39 | 88.73 | 94.72 | 0.47 | 0.00 | 3.15 | 0.00 | 0.50 |
| 12 | 0.75 | 10.18 | 3.34 | 13.52 | 92.76 | 96.45 | 0.43 | 0.00 | 0.80 | 0.87 | 1.14 |
| 9 | 1.00 | 11.65 | 0.00 | 11.65 | 73.36 | 92.29 | 1.56 | 3.08 | 2.27 | 0.36 | |

As shown in Tab. 4, reasonable HIBA conversions are not achieved until a molar ratio of methanol to HIBA of 5. On the other hand, the selectivities are significantly higher in the presence of water, even in the case of high molar ratios of methanol to HIBA.

EXAMPLES 14-19

Examples 14-19 were conducted analogously to Example 1, except that the overall feed was subjected to a preliminary purification by means of ion exchangers prior to feeding into the plant. For this purpose, the HIBA, MeOH and water components were mixed in the desired molar compositions and fed continuously to a cationic ion exchanger (Lewatit K2341). The loading was adjusted to 43.3 g of feed solution per h and g of ion exchanger. The treatment was conducted until the pH at the outlet of the ion exchanger column was 4±0.1. The feed solution thus treated was then fed into the evaporator. The resulting values are shown in Tab. 5.

TAB. 5

Treatment with ion exchanger

| Example | Molar MeOH:HIBA ratio | HIBA % by wt. | MeOH % by wt. | Water % by wt. | HIBA conversion % | MHIB yield % | MHIB selectivity % |
|---|---|---|---|---|---|---|---|
| 14 | 4 | 42.9 | 53.3 | 3.8 | 90.0 | 87.5 | 97.2 |
| 15 | 6 | 33.9 | 63.2 | 3.0 | 92.7 | 91.0 | 98.2 |
| 16 | 8 | 28.0 | 69.6 | 2.4 | 94.2 | 92.3 | 98.0 |
| 17 | 12 | 20.8 | 77.4 | 1.8 | 96.2 | 93.6 | 97.3 |
| 18 | 15 | 17.4 | 81.1 | 1.5 | 96.9 | 95.2 | 98.2 |
| 19 | 20 | 13.7 | 85.1 | 1.2 | 97.7 | 95.8 | 98.1 |

Much higher selectivities in terms of MHIB are achieved than without pretreatment with ion exchanger (Tab. 4).

The invention claimed is:

1. A process for preparing alpha-hydroxycarboxylic esters, the process comprising:
    performing an alcoholysis reaction of an alpha-hydroxycarboxamide and an alcohol in a gas phase in the presence of a heterogeneous catalyst,
    wherein a molar ratio of the alcohol to the alpha-hydroxycarboxamide is 2-25 mol/mol, and
    wherein the alcoholysis reaction is performed in the presence of 0.01-10 mol/mol of water relative to the alpha-hydroxycarboxamide.

2. The process according to claim 1, wherein the catalyst is a zirconium dioxide catalyst.

3. The process according to claim 1, wherein the alcoholysis reaction is performed at a reaction temperature of 150-300° C.

4. The process according to claim 1, further comprising treating the alpha-hydroxycarboxamide, the alcohol, or both with a cationic ion exchanger prior to the performing of the alcoholysis reaction in the gas phase.

5. The process according to claim 1, wherein the alpha-hydroxycarboxamide is hydroxyisobutyramide and the alcohol is methanol.

6. The process according to claim 1, wherein ammonia is formed and the process further comprises feeding the ammonia into a hydrogen cyanide preparation process or an ammoxidation process.

* * * * *